(12) United States Patent
Yu et al.

(10) Patent No.: US 8,114,443 B2
(45) Date of Patent: Feb. 14, 2012

(54) PHYTASE-EXPRESSING TRANSGENIC PLANTS

(75) Inventors: Su-May Yu, Taipei (TW); Ya-Fang Hong, Kaohsiung (TW)

(73) Assignee: Academia Sinica, Taipei (TW)

( * ) Notice: Subject to any disclaimer, the term of this patent is extended or adjusted under 35 U.S.C. 154(b) by 734 days.

(21) Appl. No.: 12/055,502

(22) Filed: Mar. 26, 2008

(65) Prior Publication Data

US 2009/0092703 A1  Apr. 9, 2009

Related U.S. Application Data

(63) Continuation-in-part of application No. 10/989,719, filed on Nov. 15, 2004, now Pat. No. 7,411,115, which is a continuation-in-part of application No. 10/097,896, filed on Mar. 13, 2002, now abandoned.

(51) Int. Cl.
*A61K 38/00* (2006.01)
*A01H 1/00* (2006.01)
*C07H 21/04* (2006.01)
*C07K 14/415* (2006.01)
*C12N 15/00* (2006.01)

(52) U.S. Cl. ....... 424/725; 424/93.7; 424/94.1; 435/6.1; 435/69.1; 435/468; 435/419; 435/320.1; 536/24.1; 800/278; 800/295; 530/370

(58) Field of Classification Search .............. 435/6, 69.1, 435/468, 419, 320.1, 6.1; 536/24.1; 800/278, 800/295; 530/370; 424/93.7, 94.1, 725
See application file for complete search history.

(56) References Cited

U.S. PATENT DOCUMENTS

| 5,593,963 | A | 1/1997 | Van Ooijen et al. |
| 5,770,413 | A | 6/1998 | Van Ooijen et al. |
| 5,900,525 | A | 5/1999 | Austin-Phillips et al. |
| 6,303,766 | B1 | 10/2001 | Grabau et al. |
| 2006/0137038 | A1* | 6/2006 | Lanahan et al. ............. 800/278 |
| 2006/0141562 | A1* | 6/2006 | Blattmann et al. ........... 435/69.1 |
| 2006/0228400 | A1* | 10/2006 | Lanahan et al. ............. 424/442 |

FOREIGN PATENT DOCUMENTS

WO  WO 01/22806  4/2001

OTHER PUBLICATIONS

El-Sharkawy, Mabrouk A., "Cassava Biology and Physiology," *Plant Molecular Biology*, 56:481-501 (2004).
Gaston et al., "Phosphorous Runoff Relationship for Louisiana Coastal Plain Soils Amended with Poultry Litter," *J. Environ. Qual.* 32:1422-1429 (2003).
Lahai et al., "Leaf Chlorophyll Content and Tuberous Root Yield of Cassava in Inland Valley," *African Crop Science Journal*, 11(2):107-117 (2003).
Moussa et al., "Co2 Fixation and Translocation of Photoassimilates as Selection Criteria of Egypian Taro Genotypes," *Journal of Integrative Plant Biology*, 48(5):563-566 (2006).
Oyetunji et al., "The Relationships Between Relative Water Content, Chlorophyll Synthesis and Yield Performance of Yam (*Dioscorea rotundata*) as affected by Soil Amendments and Mycorrhizal Inoculation," *Archives of Agronomy and Soil Science*, 53(3):335-344 (2007) (Abstract only).
Pote et al., "Water-Quality Effects of Incorporating Poultry Litter into Perennial Grassland Soils," *J. Environ. Qual.* 32:2392-2398 (2003).

* cited by examiner

*Primary Examiner* — Phuong Bui
(74) *Attorney, Agent, or Firm* — Occhiuti Rohlicek & Tsao LLP

(57) ABSTRACT

Disclosed are a transgenic plant and a transformed plant cell containing a heterologous nucleic acid that includes a sweet potato sporamin SPO promoter operably linked to a sequence encoding a polypeptide. Also disclosed are uses of the plant or cell.

21 Claims, 1 Drawing Sheet pSpo-appA

SEQUENCE LISTING

```
<160> NUMBER OF SEQ ID NOS: 19

<210> SEQ ID NO 1
<211> LENGTH: 1059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aagctttgcc aaacagagcc taaatccatc atttggattc aacttatgtg aatgaaagag      60 aggggggcgaa aagttagctt aattttacta atttgggttt ttatttccaa aggccagagg    120
aaggaaaaag aaaattaaaa gacatggctc tccatcgggt tgcactccac ccgtgtgcag    180
gacaactttt acgttataca atgcaaactc ctttaaaata aattaaaatc atatatatat    240
aaaatagtgc aacctatatc actttctcaa tgtgggacga aggcactttc aaaagtcttt    300
cgaatcctat ttttccttga atatatttcg agaataaatt tttcaattaa tcatcattat    360
ccatctacgt gtatatatat aatatatatt tcaaattaaa catctaactt agattttcca    420
aaaaaaaaaa acatctaact tagaagaacc caaatttatt tttaactcta cctatatcaa    480
aagtggactc tactgaaaat tataccacaa aatgatcatt ttaaatgtta tttttaacaa    540 aaatttaga  cattatctta ttttaatctt ctaccggtta gaatactgaa ataaatttca    600
ctcataacat aaatttgact agtgatcgtg aattttttacg taaattaatc aaataattgt    660
atgtaatgca atggattttg atgatgggta aaatttgatg atgggtaaaa tatattttaa    720
ttattacact acttgccttc tttgttccta ggatcataga cttcacctat agtaaaacca    780
ttggacactt gggcggccac aaatcatttc tattatttct cccaaatcat ttctgttatc    840
```

| aactctatct cacccataa gacaccgtaa gtgtcccatc catcggtcga tcactgtgta | 900 |
| gttaaatctt caagtagcta agtaattgtg tttcgcgatg aaaattctga atacaaaaag | 960 |
| agaaaagcaa aataatctta aagttgtaca agaaacaata attcaacctt atctcttgtt | 1020 |
| gtctataaat tggatgcatg catgagacta tgagagccc | 1059 |

<210> SEQ ID NO 2  
<211> LENGTH: 1131  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 2

| aagctttgcc aaacagagcc taaatccatc atttggattc aacttatgtg aatgaaagag | 60 |
| aggggggcgaa aagttagctt aattttacta atttgggttt ttatttccaa aggccagagg | 120 |
| aaggaaaaag aaaattaaaa gacatggctc tccatcgggt tgcactccac ccgtgtgcag | 180 |
| gacaactttt acgttataca atgcaaactc ctttaaaata aattaaaatc atatatatat | 240 |
| aaaatagtgc aacctatatc actttctcaa tgtgggacga aggcactttc aaaagtcttt | 300 |
| cgaatcctat ttttccttga atatatttcg agaataaatt tttcaattaa tcatcattat | 360 |
| ccatctacgt gtatatatat aatatatatt tcaaattaaa catctaactt agattttcca | 420 |
| aaaaaaaaaa acatctaact tagaagaacc caaatttatt tttaactcta cctatatcaa | 480 |
| aagtggactc tactgaaaat tataccacaa aatgatcatt ttaaatgtta tttttaacaa | 540 |
| aaattttaga cattatctta ttttaatctt ctaccggtta gaatactgaa ataaatttca | 600 |
| ctcataacat aaatttgact agtgatcgtg aattttttacg taaattaatc aaataattgt | 660 |
| atgtaatgca atggattttg atgatgggta aaatttgatg atgggtaaaa tatatttaa | 720 |
| ttattacact acttgccttc tttgttccta ggatcataga cttcacctat agtaaaacca | 780 |
| ttggacactt gggcggccac aaatcatttc tattatttct cccaaatcat ttctgttatc | 840 |
| aactctatct cacccataa gacaccgtaa gtgtcccatc catcggtcga tcactgtgta | 900 |
| gttaaatctt caagtagcta agtaattgtg tttcgcgatg aaaattctga atacaaaaag | 960 |
| agaaaagcaa aataatctta aagttgtaca agaaacaata attcaacctt atctcttgtt | 1020 |
| gtctataaat tggatgcatg catgagacta tgagagccca tcacaacaca ccaacaaatt | 1080 |
| aaacatcatt acctcttagc tttctcccaa gttgtcatct catctgccac c | 1131 |

<210> SEQ ID NO 3  
<211> LENGTH: 1242  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 3

| aagctttgcc aaacagagcc taaatccatc atttggattc aacttatgtg aatgaaagag | 60 |
| aggggggcgaa aagttagctt aattttacta atttgggttt ttatttccaa aggccagagg | 120 |
| aaggaaaaag aaaattaaaa gacatggctc tccatcgggt tgcactccac ccgtgtgcag | 180 |
| gacaactttt acgttataca atgcaaactc ctttaaaata aattaaaatc atatatatat | 240 |
| aaaatagtgc aacctatatc actttctcaa tgtgggacga aggcactttc aaaagtcttt | 300 |
| cgaatcctat ttttccttga atatatttcg agaataaatt tttcaattaa tcatcattat | 360 |

-continued

```
ccatctacgt gtatatatat aatatatatt tcaaattaaa catctaactt agattttcca    420
aaaaaaaaaa acatctaact tagaagaacc caaatttatt tttaactcta cctatatcaa    480
aagtggactc tactgaaaat tataccacaa aatgatcatt ttaaatgtta tttttaacaa    540 aaatttaga cattatctta ttttaatctt ctaccggtta gaatactgaa ataaatttca     600
ctcataacat aaatttgact agtgatcgtg aattttacg taaattaatc aaataattgt     660
atgtaatgca atggattttg atgatgggta aaatttgatg atgggtaaaa tatatttaa    720 ttattacact acttgccttc tttgttccta ggatcataga cttcacctat agtaaaacca    780
ttggacactt gggcggccac aaatcatttc tattatttct cccaaatcat ttctgttatc    840
aactctatct caccccataa gacaccgtaa gtgtcccatc catcggtcga tcactgtgta    900
gttaaatctt caagtagcta agtaattgtg tttcgcgatg aaaattctga atacaaaaag    960
agaaaagcaa aataatctta aagttgtaca agaaacaata attcaacctt atctcttgtt   1020
gtctataaat tggatgcatg catgagacta tgagagccca tcacaacaca ccaacaaatt   1080
aaacatcatt acctcttagc tttctcccaa gttgtcatct catctgccac catgaaagcc   1140
ctcacactcg cacttttctt agctctttcc ctctatctcc tccccaatcc agcccattcc   1200
aggttcaatc ccatccgcct ccccaccaca cacgaacccg cc                      1242
```

<210> SEQ ID NO 4
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Pro Val Lys Leu Gly Trp Leu Thr Pro Arg Gly Gly Glu Leu Ile Ala
1               5                   10                  15

Tyr Leu Gly His Tyr Gln Arg Gln Arg Leu Val Ala Asp Gly Leu Leu
            20                  25                  30

Ala Lys Lys Gly Cys Pro Gln Ser Gly Gln Val Ala Ile Ile Ala Asp
        35                  40                  45

Val Asp Glu Arg Thr Arg Lys Thr Gly Glu Ala Phe Ala Ala Gly Leu
    50                  55                  60

Ala Pro Asp Cys Ala Ile Thr Val His Thr Gln Ala Asp Thr Ser Ser
65                  70                  75                  80

Pro Asp Pro Leu Phe Asn Pro Leu Lys Thr Gly Val Cys Gln Leu Asp
                85                  90                  95

Asn Ala Asn Val Thr Asp Ala Ile Leu Ser Arg Ala Gly Gly Ser Ile
            100                 105                 110

Ala Asp Phe Thr Gly His Arg Gln Thr Ala Phe Arg Glu Leu Glu Arg
        115                 120                 125

Val Leu Asn Phe Pro Gln Ser Asn Leu Cys Leu Lys Arg Glu Lys Gln
    130                 135                 140

Asp Glu Ser Cys Ser Leu Thr Gln Ala Leu Pro Ser Glu Leu Lys Val
145                 150                 155                 160

Ser Ala Asp Asn Val Ser Leu Thr Gly Ala Val Ser Leu Ala Ser Met
                165                 170                 175

Leu Thr Glu Ile Phe Leu Leu Gln Gln Ala Gln Gly Met Pro Glu Pro
            180                 185                 190

Gly Trp Gly Arg Ile Thr Asp Ser His Gln Trp Asn Thr Leu Leu Ser
        195                 200                 205
```

Leu His Asn Ala Gln Phe Tyr Leu Leu Gln Arg Thr Pro Glu Val Ala
    210                 215                 220

Arg Ser Arg Ala Thr Pro Leu Leu Asp Leu Ile Lys Thr Ala Leu Thr
225                 230                 235                 240

Pro His Pro Pro Gln Lys Gln Ala Tyr Gly Val Thr Leu Pro Thr Ser
                245                 250                 255

Val Leu Phe Ile Ala Gly His Asp Thr Asn Leu Ala Asn Leu Gly Gly
            260                 265                 270

Ala Leu Glu Leu Asn Trp Thr Leu Pro Gly Gln Pro Asp Asn Thr Pro
        275                 280                 285

Pro Gly Gly Glu Leu Val Phe Glu Arg Trp Arg Arg Leu Ser Asp Asn
    290                 295                 300

Ser Gln Trp Ile Gln Val Ser Leu Val Phe Gln Thr Leu Gln Gln Met
305                 310                 315                 320

Arg Asp Lys Thr Pro Leu Ser Leu Asn Thr Pro Pro Gly Glu Val Lys
                325                 330                 335

Leu Thr Leu Ala Gly Cys Glu Glu Arg Asn Ala Gln Gly Met Cys Ser
            340                 345                 350

Leu Ala Gly Phe Thr Gln Ile Val Asn Glu Ala Arg Ile Pro Ala Cys
        355                 360                 365

Ser Leu
    370

<210> SEQ ID NO 5
<211> LENGTH: 1113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ccggtaaaac tgggttggct gacaccgcgt ggtggtgagc taatcgccta tctcggacat      60
taccaacgcc agcgtctggt agccgacgga ttgctggcga aaaagggctg cccgcagtct     120
ggtcaggtcg cgattattgc tgatgtcgac gagcgtaccc gtaaaacagg cgaagccttc     180
gccgccgggc tggcacctga ctgtgcaata accgtacata cccaggcaga tacgtccagt     240
cccgatccgt tatttaatcc tctaaaaact ggcgtttgcc aactggataa cgcgaacgtg     300
actgacgcga tcctcagcag ggcaggaggg tcaattgctg actttaccgg catcggcaa     360 acggcgtttc gcgaactgga acgggtgctt aattttccgc aatcaaactt gtgccttaaa     420
cgtgagaaac aggacgaaag ctgttcatta acgcaggcat taccatcgga actcaaggtg     480
agcgccgaca atgtctcatt aaccggtgcg gtaagcctcg catcaatgct gacgagata      540 tttctcctgc aacaagcaca gggaatgccg gagccggggt ggggaaggat caccgattca     600
caccagtgga acaccttgct aagtttgcat aacgcgcaat tttatttgct caacgcacg      660 ccagaggttg cccgcagccg cgccaccccg ttattagatt tgatcaagac agcgttgacg     720
ccccatccac cgcaaaaaca ggcgtatggt gtgacattac ccacttcagt gctgtttatc     780
gccggacacg atactaatct ggcaaatctc ggcggcgcac tggagctcaa ctggacgctt     840
cccggtcagc cggataacac gccgccaggt ggtgaactgg tgtttgaacg ctggcgtcgg     900
ctaagcgata cagccagtg gattcaggtt cgctggtct tccagacttt acagcagatg      960
cgtgataaaa cgccgctgtc attaaatacg ccgcccggag aggtgaaact gaccctggca    1020
ggatgtgaag agcgaaatgc gcagggcatg tgttcgttgg caggttttac gcaaatcgtg    1080

```
                                                              -continued
aatgaagcac gcataccggc gtgcagtttg taa                              1113
```

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
His Ser Arg Phe Asn Pro Ile Arg Leu Pro Thr Thr His Glu Pro Ala
1               5                   10                  15
```

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
atgaaagccc tcacactcgc actttttctta gctctttccc tctatctcct ccccaatcca    60
gcc                                                                   63
```

<210> SEQ ID NO 8
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Lys Ala Leu Thr Leu Ala Leu Phe Leu Ala Leu Ser Leu Tyr Leu
1               5                   10                  15

Leu Pro Asn Pro Ala His Ser Arg Phe Asn Pro Ile Arg Leu Pro Thr
            20                  25                  30

Thr His Glu Pro Ala Pro Val Lys Leu Gly Trp Leu Thr Pro Arg Gly
        35                  40                  45

Gly Glu Leu Ile Ala Tyr Leu Gly His Tyr Gln Arg Gln Arg Leu Val
    50                  55                  60

Ala Asp Gly Leu Leu Ala Lys Lys Gly Cys Pro Gln Ser Gly Gln Val
65                  70                  75                  80

Ala Ile Ile Ala Asp Val Asp Glu Arg Thr Arg Lys Thr Gly Glu Ala
                85                  90                  95

Phe Ala Ala Gly Leu Ala Pro Asp Cys Ala Ile Thr Val His Thr Gln
            100                 105                 110

Ala Asp Thr Ser Ser Pro Asp Pro Leu Phe Asn Pro Leu Lys Thr Gly
        115                 120                 125

Val Cys Gln Leu Asp Asn Ala Asn Val Thr Asp Ala Ile Leu Ser Arg
    130                 135                 140

Ala Gly Gly Ser Ile Ala Asp Phe Thr Gly His Arg Gln Thr Ala Phe
145                 150                 155                 160

Arg Glu Leu Glu Arg Val Leu Asn Phe Pro Gln Ser Asn Leu Cys Leu
                165                 170                 175

Lys Arg Glu Lys Gln Asp Glu Ser Cys Ser Leu Thr Gln Ala Leu Pro
            180                 185                 190

Ser Glu Leu Lys Val Ser Ala Asp Asn Val Ser Leu Thr Gly Ala Val
        195                 200                 205
```

```
Ser Leu Ala Ser Met Leu Thr Glu Ile Phe Leu Leu Gln Gln Ala Gln
    210                 215                 220

Gly Met Pro Glu Pro Gly Trp Gly Arg Ile Thr Asp Ser His Gln Trp
225                 230                 235                 240

Asn Thr Leu Leu Ser Leu His Asn Ala Gln Phe Tyr Leu Leu Gln Arg
                245                 250                 255

Thr Pro Glu Val Ala Arg Ser Arg Ala Thr Pro Leu Leu Asp Leu Ile
            260                 265                 270

Lys Thr Ala Leu Thr Pro His Pro Gln Lys Gln Ala Tyr Gly Val
        275                 280                 285

Thr Leu Pro Thr Ser Val Leu Phe Ile Ala Gly His Asp Thr Asn Leu
    290                 295                 300

Ala Asn Leu Gly Gly Ala Leu Glu Leu Asn Trp Thr Leu Pro Gly Gln
305                 310                 315                 320

Pro Asp Asn Thr Pro Pro Gly Gly Glu Leu Val Phe Glu Arg Trp Arg
                325                 330                 335

Arg Leu Ser Asp Asn Ser Gln Trp Ile Gln Val Ser Leu Val Phe Gln
            340                 345                 350

Thr Leu Gln Gln Met Arg Asp Lys Thr Pro Leu Ser Leu Asn Thr Pro
        355                 360                 365

Pro Gly Glu Val Lys Leu Thr Leu Ala Gly Cys Glu Glu Arg Asn Ala
    370                 375                 380

Gln Gly Met Cys Ser Leu Ala Gly Phe Thr Gln Ile Val Asn Glu Ala
385                 390                 395                 400

Arg Ile Pro Ala Cys Ser Leu
                405

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cattccaggt tcaatcccat ccgcctcccc accacacacg aacccgcc                 48

<210> SEQ ID NO 10
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atcacaacac accaacaaat taaacatcat tacctcttag ctttctccca agttgtcatc    60
tcatctgcca cc                                                        72

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Lys Ala Leu Thr Leu Ala Leu Phe Leu Ala Leu Ser Leu Tyr Leu
```

```
1               5                  10                 15
```

Leu Pro Asn Pro Ala
          20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccaagcttt gccaaacaga gccta                                          25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaattcggc gggttcgtgt gtggt                                          25

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccgagctgc agatcgttca aacattt                                        27

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agcgagctcg atcgatctct agacat                                         26

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagaattcc agagtgagcc ggagctgaag ct                                  32

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

-continued

```
aaactgcagt tacaaactgc acgccggtat                                    30

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgaattcca gagtgagccg gagctg                                        26

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctctagata cgcattagac agttcttcgt t                                  31
```

PHYTASE-EXPRESSING TRANSGENIC PLANTS

RELATED APPLICATIONS

This application is a continuation-in-part of and claims priority to U.S. application Ser. No. 10/989,719, filed Nov. 15, 2004, which is a continuation-in-part of and claims priority to U.S. application Ser. No. 10/097,896, filed Mar. 13, 2002. The contents of the two applications are incorporated herein by reference.

BACKGROUND

Phytase is an enzyme that sequentially removes phosphates from the phytate molecule. Phytate (myo-inositol hexakisphosphate) is the principal storage form of phosphorus in many plant tissues such as bran and seeds.

Phosphorus is an essential and limiting nutrient for growth and development of plants. To increase crop yield, large amount of phosphorus fertilizers are applied to cropland each year. However, only 10-20% of the fertilizer is utilized (Holford, 1997, Aust J Soil Res 35: 227-23). The rest of the phosphorus becomes fixed in form and is poorly available to plants (Vance et al., 2003, New Phytol 157: 423-447). The increased soil phosphorous level eventually leads to contamination to water. As phosphorous is a limiting nutrient for aquatic plants as well, an increased water phosphorous level result in eutrophication and decreased water quality. Thus, the large input of phosphorus fertilizer is not only expensive but also nonsustainable.

Phosphorus is an essential dietary requirement for growth and development of animals. Bran and seeds, rich in phytate, constitute major components of animal feeds. However, non-ruminant animals utilize phytate poorly due to the absence of gastrointestinal tract phytase. As a result, non-utilized phytate is excreted by the animals. To cope with the problems, swine and poultry rations are routinely supplemented with inorganic phosphorous or phytase. However, neither approach is satisfactory. In the former, the supplement increases feed costs and increases the phosphorous content in animal waste; in the latter, phytase is expensive and unstable. Animal waste or manure has long been applied as fertilizer to pastures and croplands. Because of phosphorous content in the waste, this practice increases soil phosphorous levels and, eventually, leads to eutrophication.

In the United States, the swine and poultry industries annually generate over 20 million tons of manure containing over 300,000 tons of waste phosphorous (Cromwell et al., Altech Conference Proceedings, 1991). As phosphorus recycles among plants, animals, soil and water, organic phosphorus could make up 20-80% of the total phosphorus in soil and phytate accounts for up to half of the soil organic phosphorus (Dalal, 1977, Adv Agron 29: 83-117). The resulting high soil phosphorus levels pose a server environmental threat.

Thus, there are needs for new, cheap, absorbable phosphorus sources for animals and plants, and needs for means to deal with eutrophication and related environment problems.

SUMMARY

This invention relates to a transgenic plant, which can be used to deal with the problems described above. The plant has a genome that comprises a heterologous nucleic acid containing a promoter region operably linked to a sequence encoding a polypeptide having phytase activity. The promoter region includes the sequence of SEQ ID NO: 1:

```
                                             (SEQ ID NO: 1)
-1059 aagctttgccaaacagagcctaaatccatcatttggattcaact tatgtgaatgaaagagagggggcgaaaagttagcttaattttactaattt gggtttttatttccaaaggccagaggaaggaaaaagaaaattaaaagaca tggctctccatcgggttgcactccacccgtgtgcaggacaacttttacgt tatacaatgcaaactcctttaaaataaattaaaatcatatatatataaaa tagtgcaacctatatcactttctcaatgtgggacgaaggcactttcaaaa gtctttcgaatcctattttccttgaatatatttcgagaataaattttc aattaatcatcattatccatctacgtgtatatatataatatatatttcaa attaaacatctaacttagattttccaaaaaaaaaaacatctaacttaga agaacccaaatttattttaactctacctatatcaaaagtggactctact gaaaattataccacaaaatgatcattttaaatgttattttaacaaaaat tttagacattatcttatttaatcttctaccggttagaatactgaaataa atttcactcataacataaatttgactagtgatcgtgaattttacgtaaa ttaatcaaataattgtatgtaatgcaatggattttgatgatgggtaaaat ttgatgatgggtaaaatatattttaattattacactacttgccttctttg ttcctaggatcatagacttcacctatagtaaaaccattggacacttgggc ggccacaaatcatttctattatttctcccaaatcatttctgttatcaact ctatctcaccccataagacaccgtaagtgtcccatccatcggtcgatcac tgtgtagttaaatcttcaagtagctaagtaattgtgtttcgcgatgaaaa ttctgaatacaaaaagagaaaagcaaaataatcttaaagttgtacaagaa acaataattcaaccttatctcttgttgtctataaattggatgcatgcatg agactatgagagccc -1
```

The transgenic plant can be any suitable plant such as a tuberous plant. Examples of the tuberous plant include potato, sweet potato, cassava, carrot, yam, taro, onion, and lily. In a preferred embodiment, the tuberous plant is a potato. The heterologous nucleic acid region can include SEQ ID NO: 2 or 3.

```
                                             (SEQ ID NO: 3)
aagctttgccaaacagagcctaaatccatcatttggattcaacttatgtg aatgaaagagaggggcgaaaagttagcttaattttactaatttgggttt ttatttccaaaggccagaggaaggaaaaagaaaattaaaagacatggctc tccatcgggttgcactccacccgtgtgcaggacaacttttacgttataca atgcaaactcctttaaaataaattaaaatcatatatatataaaatagtgc aacctatatcactttctcaatgtgggacgaaggcactttcaaaagtcttt cgaatcctattttccttgaatatatttcgagaataaattttcaattaa tcatcattatccatctacgtgtatatatataatatatatttcaaattaaa catctaacttagattttccaaaaaaaaaaacatctaacttagaagaacc caaatttattttaactctacctatatcaaaagtggactctactgaaaat tataccacaaaatgatcattttaaatgttattttaacaaaaatttaga cattatcttatttaatcttctaccggttagaatactgaaataaatttca ctcataacataaatttgactagtgatcgtgaattttacgtaaattaatc
```

-continued
```
aaataattgtatgtaatgcaatggattttgatgatgggtaaaatttgatg atgggtaaaatatattttaattattacactacttgccttctttgttccta ggatcatagacttcacctatagtaaaaccattggacacttgggcggccac aaatcatttctattatttctcccaaatcatttctgttatcaactctatct cacccataagacaccgtaagtgtcccatccatcggtcgatcactgtgta gttaaatcttcaagtagctaagtaattgtgtttcgcgatgaaaattctga atacaaaagagaaaagcaaaataatcttaaagttgtacaagaaacaata attcaaccttatctcttgttgtctataaattggatgcatgcatgagacta tgagagccatcacaacacaccaacaaattaaacatcattacctcttaac tttctcccaaattatcatctcatctgccaccATGAAAGCCCTCACACTCG

CACTTTTCTTAGCTCTTTCCCTCTATCTCCTCCCCAATCCAGCCCATTCC

AGGTTCAATCCCATCCGCCTCCCCACCACACACGAACCCGCC
```

The sequence of SEQ ID NO: 3 includes four segments: SEQ ID NO: 1 mentioned above, a 5' un-translated region (5' UTR) from a sweet potato sporamin gene (underlined; SEQ ID NO: 10), a sequence encoding a signal peptide (upper case only; SEQ ID NO: 7), and an extra sequence (upper case and underlined: CATTCCAGGTTCAATCCCATCC-GCCTC-CCC-ACCACACACGAACCCGCC; SEQ ID NO: 9). The first two segments (those in lower case) form SEQ ID NO: 2, which is a non-encoding region of 1131 bp in length. The signal peptide encoding sequence (atgaaagccctcacactcg-cacttttcttagctctttccctctatctcctcccc-aatccagcc, SEQ ID NO: 7) encodes MKALTLALFLALSLYLLPNPA (SEQ ID NO:11). The extra sequence encodes HSRFNPIRLPTTHEPA (SEQ ID NO: 6). Other suitable signal peptide sequences or extra sequences (e.g., fragments or fusion proteins them) can be used in this invention. The polypeptide having phytase activity can include SEQ ID NO: 4. Shown below are the sequences for SEQ ID NO:4 and a nucleic acid encoding it (SEQ ID NO:5).

```
                                          (SEQ ID NO: 4)
PVKLGWLTPRGGELIAYLGHYQRQRLVADGLLAKKGCPQSGQVAIIADVD

ERTRKTGEAFAAGLAPDCAITVHTQADTSSPDPLFNPLKTGVCQLDNANV

TDAILSRAGGSIADFTGHRQTAFRELERVLNFPQSNLCLKREKQDESCSL

TQALPSELKVSADNVSLTGAVSLASMLTEIFLLQQAQGMPEPGWGRITDS

HQWNTLLSLHNAQFYLLQRTPEVARSRATPLLDLIKTALTPHPPQKQAYG

VTLPTSVLFIAGHDTNLANLGGALELNWTLPGQPDNTPPGGELVFERWRR

LSDNSQWIQVSLVFQTLQQMRDKTPLSLNTPPGEVKLTLAGCEERNAQGM

CSLAGFTQIVNEARIPACSL
                                          (SEQ ID NO: 5)
ccggtaaaactgggttggctgacaccgcgtggtggtgagctaatcgccta tctcggacattaccaacgccagcgtctggtagccgacggattgctggcga aaaagggctgcccgcagtctggtcaggtcgcgattattgctgatgtcgac gagcgtacccgtaaaacaggcgaagccttcgccgccgggctggcacctga ctgtgcaataaccgtacatacccaggcagatacgtccagtcccgatccgt tatttaatcctctaaaaactggcgtttgccaactggataacgcgaacgtg
```

```
actgacgcgatcctcagcagggcaggagggtcaattgctgactttaccgg gcatcggcaaacggcgtttcgcgaactggaacgggtgcttaattttccgc aatcaaacttgtgccttaaacgtgagaaacaggacgaaagctgttcatta acgcaggcattaccatcggaactcaaggtgagcgccgacaatgtctcatt aaccggtgcggtaagcctcgcatcaatgctgacggagatatttctcctgc aacaagcacagggaatgccggagccggggtggggaaggatcaccgattca caccagtggaacaccttgctaagtttgcataacgcgcaattttatttgct acaacgcacgccagaggttgcccgcagccgcgccacccccgttattagatt tgatcaagacagcgttgacgccccatccaccgcaaaaacaggcgtatggt gtgacattacccacttcagtgctgtttatcgccggacacgatactaatct ggcaaatctcggcggcgcactggagctcaactggacgcttcccggtcagc cggataacacgccgccaggtggtgaactggtgtttgaacgctggcgtcgg ctaagcgataacagccagtggattcaggtttcgctggtcttccagacttt acagcagatgcgtgataaaacgccgctgtcattaaatacgccgcccggag aggtgaaactgaccctggcaggatgtgaagagcgaaatgcgcagggcatg tgttcgttggcaggttttacgcaaatcgtgaatgaagcacgcataccggc gtgcagtttgtaa
```

In one example, the polypeptide having phytase activity includes SEQ ID NO: 8 (shown below). In this polypeptide, the above-mentioned signal peptide and the extra sequence (underlined) is fused to the amino-terminus of the polypeptide having phytase activity.

```
                                          (SEQ ID NO: 8)
MKALTLALFLALSLYLLPNPAHSRFNPIRLPTTHEPAPVKLGWLTPRGGE

LIAYLGHYQRQRLVADGLLAKKGCPQSGQVAIIADVDERTRKTGEAFAAG

LAPDCAITVHTQADTSSPDPLFNPLKTGVCQLDNANVTDAILSRAGGSIA

DFTGHRQTAFRELERVLNFPQSNLCLKREKQDESCSLTQALPSELKVSAD

NVSLTGAVSLASMLTEIFLLQQAQGMPEPGWGRITDSHQWNTLLSLHNAQ

FYLLQRTPEVARSRATPLLDLIKTALTPHPPQKQAYGVTLPTSVLFIAGH

DTNLANLGGALELNWTLPGQPDNTPPGGELVFERWRRLSDNSQWIQVSLV

FQTLQQMRDKTPLSLNTPPGEVKLTLAGCEERNAQGMCSLAGFTQIVNEA

RIPACSL
```

The above-described transgenic plant has an increased leaf chlorophyll or chloroplast content as compared with a second plant. The second plant is identical to the transgenic plant except that the second plant does not have the polypeptide having phytase activity. In the case of a transgenic tuberous plant, the transgenic tuberous plant have a larger number of tuber or a larger tuber yield than a second tuberous plant, which is identical to the transgenic plant except that the second plant does not have the polypeptide having phytase activity. The chlorophyll or chloroplast content, number of tuber, and tuber yield can be determined by standard methods or in the manner described in the examples below.

In another aspect, the invention features a transformed plant cell that includes the above-mentioned heterologous nucleic acid. The transformed plant cell can be a tuberous plant cell, such as a cell of potato, sweet potato, cassava, carrot, yam, taro, onion, or lily. In one embodiment, the cell is a potato cell. Such a cell can be used to generate the transgenic plant mentioned above.

The invention features a method of producing the above-mentioned transgenic plant. The method includes stably transforming a plant cell or plant part with the above mentioned heterologous nucleic acid; selecting a transformed plant cell or plant part in a selection medium, and cultivating the transformed cell or plant part in a medium to generate a transgenic plant.

In a further aspect, the invention features an isolated nucleic acid comprising SEQ ID NO: 1 and a vector comprising the nucleic acid, where the nucleic acid is operably linked to a heterologous nucleic acid encoding a polypeptide. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express a useful polypeptide, e.g., phytase, in a plant. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A regulatory sequence includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce a useful polypeptide. Also within the scope of this invention is a host cell that contains the above-described nucleic acid. Examples include *E. coli* cells, plant cells, insect cells (e.g., using baculovirus expression vectors), yeast cells, or mammalian cells.

The above-described transgenic plant can be used in animal feed, which improves phosphorus uptake by an animal and reduces phosphorus content in animal waste. Accordingly, the invention features an animal feed composition containing the above-described transgenic plant or a plant cell thereof or a plant part thereof. Within the scope of this invention is a method for improving phosphorus uptake by an animal by feeding the feed composition to the animal. Examples of the animal include non-ruminants and ruminants (e.g., young calves) that need phosphorus. Examples of non-ruminants include monogastic animals, such as pigs or swine, poultry (e.g., chicken, duck, and turkeys), fish, and fur animals (e.g., mink and fox).

In yet a further aspect, the invention features a method for phytoremediation of a medium having an excessive level of phosphorus (e.g., phytate). The method includes the step of contacting the above-described transgenic plant with the medium. The plant can be grown in the medium. Phytase expressed and secreted by the plant enters into the medium and coverts phytate to inositol and phosphates, which can be absorbed by the transgenic plant and other plants co-cultivated with it. The medium can include soil, water, waste of animal farming, or industrial waste, which contains excessive level of phosphorus. An excessive level of phosphorus (e.g., phytate) refers to any level of phosphorus (e.g., phytate) that is unwanted or tends to cause eutrophication. Such a level can be determined by methods known in the art. See, e.g., Gaston et al., 2003, J Environ Qual. 2003 July-August; 32(4):1422-9. and Pote et al., 2003, J Environ Qual. 2003 November-December; 32(6):2392-8.

The details of one or more embodiments of the invention are set forth in the accompanying description below. Other advantages, features, and objects of the invention will be apparent from the detailed description and the claims.

DETAILED DESCRIPTION

Figure 1:
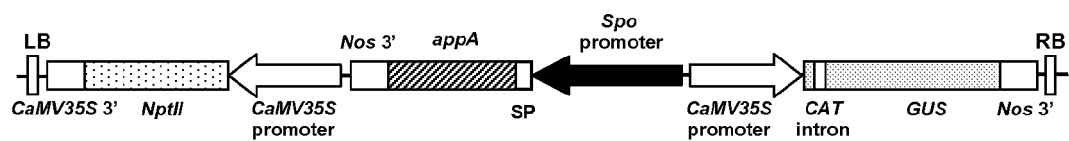
FIG. 1 is a diagram showing the construction of an exemplary expression cassette.

This invention is based, at least in part, on the unexpected discovery that ectopic overexpression of secretory phytase in transgenic plants led to improved acquisition of phosphorus (P) from phytate in a culture medium and soil. The transgenic plants had increased leaf chloroplast levels. Transgenic tuberous plants had higher tuber sizes, tuber numbers, and tuber yields than non-transgenic counterparts. The phytase-expressing transgenic plants provided an ideal feed additive for improving phytate-P digestibility in monogastric animals. In addition, the plants provided an effective means of phosphorus acquisition from organic fertilizers, and therefore can be used for phytoremediation.

Examples of the transgenic plant of this invention include, but are not limited to crops producing edible flowers such as cauliflower (*Brassica oleracea*), artichoke (*Cynara scolymus*), fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juqlans*, e.g. *regia*; peanut, *Arachis hypogeae*), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata*), tomato (*Lycopersicon*, e.g. *esculentum*), leafs, such as alfalfa (*Medicago*, e.g. *sativa*), cabbages (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. *oleraceae*), tobacco (*Nicotiana*, e.g. *tabacum*), roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*) and seeds, such as bean (*Phaseolus*, e.g. *vulgaris*), pea (*Pisum*, e.g. *sativum*), soybean (*Glycin*, e.g. *max*), wheat (*Triticum*, e.g. *aestivum*), barley (*Hordeum*, e.g. *vulgare*), corn (*Zea*, e.g. *mays*), rice (*Oryza*, e.g. *sativa*), rapeseed (*Brassica nanus*), millet (*Panicum L.*), sunflower (*Helianthus annus*), oats (*Avena sativa*), tubers, such as kohlrabi (*Brassica*, e.g. *oleraceae*), potato (*Solanum*, e.g. *tuberosum*) and the like. The choice of the plant species is primarily determined by the intended use of the plant or parts thereof and the amenability of the plant species to transformation. Several techniques are available for the introduction of the expression construct containing the phytase-encoding DNA sequence into the target plants. Such techniques include but are not limited to transformation of protoplasts using the calcium/polyethylene glycol method, electroporation and microinjection or (coated) particle bombardment.

In a preferred embodiment, the transgenic plant is a tuberous plant. A tuberous plant is a plant that produces tuberous roots, e.g., potato, sweet potato, cassava, carrot, and yam; or a plant that produces tuberous stems, e.g., taro, onion, and lily. Among the tuberous plants, potato is of particular interest as it serves as a major food crop in many countries and is widely used in food, animal feed, and other industries.

As described therein, a sweet potato sporamin SPO promoter directs high expression of a recombinant protein when it is introduced into a plant cell, for example, via *Agrobacterium*-mediated transformation. Specifically, this invention features a transformed plant cell containing a heterologous nucleic acid that includes a sweet potato sporamin promoter operably linked to a sequence encoding a polypeptide.

In one aspect, the invention features a transgenic plant, the genome of which includes a heterologous nucleic acid that contains a promoter region operably linked to a sequence encoding a polypeptide having phytase activity. The promoter region includes the sequence of SEQ ID NO: 1.

The term "heterologous" refers to portions of a nucleic acid and indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extra-chromosomal nucleic acid. In contrast, a naturally translocated piece of chromosome would not be considered heterologous in the context of this patent application, as it comprises an endogenous nucleic acid sequence that is native to the mutated cell. A heterologous nucleic acid, gene, or protein can be one that originates from a foreign species, or, if from the same species, is substantially modified from its original form. For example, a sweet potato sporamin promoter operably linked to a heterologous coding nucleic acid sequence is one form of a sequence heterologous to sweet potato or potato. If a promoter and a coding sequence are from the same species, one or both of them are substantially modified from their original forms.

A transgenic plant described in the invention can be generated by introducing into the plant or a part thereof an expression construct comprising a DNA sequence encoding a protein having phytase activity. Expression constructs are provided by the present invention for the stable transformation of plants with a gene encoding a phytase. These constructs comprise a DNA sequence encoding a phytase which is operably linked to regulatory sequences which are capable of directing the expression of phytase. These regulatory sequences may also include sequences capable of directing transcription in plants, either constitutively, or stage and/or tissue specific, depending on the use of the plant or parts thereof. The expression constructs provided may be inserted into a vector, preferably a plasmid, used in bacteria-mediated transformation of the selected plant host. The expression construct is then preferably integrated into the genome of the plant host.

A transgene is a nucleic acid sequence (encoding, e.g., one or more subject polypeptides), which is partly or entirely heterologous to a plant cell into which it is introduced, or, is homologous to an endogenous gene of the plant or cell into which it is introduced but is intended to be inserted into the plant genome in such a way as to alter the genome (e.g., it is inserted at a location which differs from that of the natural gene or its insertion results in a knockout). A transgene can include one or more operably linked transcriptional regulatory sequences (e.g., an enhancer sequence) and any other nucleic acid, such as an intron, that may be necessary for optimal expression of a nucleic acid of interest. A "transformed," "transgenic," and "recombinant" cell refer to a host cell or organism into which a heterologous nucleic acid molecule has been introduced. The nucleic acid molecule can be stably integrated into the genome generally known in the art. Accordingly, a transgenic cell is a cell containing a transgene. A transgenic plant is any plant in which one or more, or all, of the cells of the plant include a transgene. The transgene can be introduced into the cell by introduction into a precursor cell by way of deliberate genetic manipulation, such as by T-DNA mediated transfer, electroporation, or protoplast transformation. The transgene may be integrated within a chromosome, or it may be an extrachromosomally replicating DNA.

The term phytase refers to a family of enzymes which catalyze reactions involving the liberation of inorganic phosphorus from various myoinositol phosphates. DNA sequence encoding phytase may be obtained from a variety of sources such as microbial, plant or animal sources. Preferably, the DNA sequence is obtained from microbial sources such as the bacterium *E. coli* or the filamentous fungus *Aspergillus* (e.g., *Asperaillus ficuum, Aspergillus nicer, Aspergillus awamori,* and *Aspergillus nidulans.*). Examples of suitable phytases include SrPf6 from a ruminal bacterium *Selenomonas ruminantium*, (U.S. Pat. No. 5,939,303); and PhyA form *Aspergillus niger* or *Aspergillus ficuum*, (Howson and Davis, 1983, Enzyme Microb Technol 5: 377-382; U.S. Pat. No. 5,436, 156).

Various art-known techniques can be used to introduce an expression construct containing a phytase-encoding DNA sequence into target plants. Such techniques include transformation of protoplasts using the calcium/polyethylene glycol method, electroporation and microinjection or (coated) particle bombardment. In addition to these direct DNA transformation methods, transformation systems involving vectors are widely available, such as viral vectors (e.g. from the Cauliflower Mosaic Virus (CaMV) and bacterial vectors (e.g. from the genus *Agrobacterium*) (Potrykus, supra). After selection and/or screening, the protoplasts, cells or plant parts that have been transformed can be regenerated into whole plants, using methods known in the art (See, e.g., Horsch, R.

B., Fry, J. E., Hoffmann, N. L., Eichholtz, D., Rogers, S. G. & Fraley, R. T. (1985) Science 227, 1229).

The phytase should be expressed in an environment that allows for better stability or for a particular use. The choice of cellular compartments, such as cytosol, endoplasmic reticulum, vacuole, protein body or periplasmic space can be used to create such a stable environment, depending on the biophysical parameters of the phytase. Such parameters include, but are not limited to pH-optimum, sensitivity to proteases or sensitivity to the molarity of the preferred compartment. To express phytase in the cytoplasm, the expressed enzyme should not contain a secretory signal peptide or any other target sequence. For expression in chloroplasts and mitochondria the expressed enzyme should contain a specific so-called transit peptide for import into these organelles. Targeting sequences that can be attached to the enzyme of interest in order to achieve this are known in the art. See, e.g., Smeekens et al, (1990) T.I.B.S. 15, p. 73; van den Broeck et al., (1985) Nature 313, 358; Schreier et al., (1985) EMBO J. 4, 25. If the activity of the enzyme is desired in the vacuoles, a secretory signal peptide has to be present, as well as a specific targeting sequence that directs the enzyme to these vacuoles (Tague et al, (1988) Plant Phys. 86, 506). The DNA sequence encoding the enzyme of interest should be modified in such a way that the enzyme can exert its action at the desired location in the cell.

To achieve extracellular expression of the phytase, the expression construct of the present invention utilizes a secretory signal sequence. Although signal sequences which are homologous (native) to the plant host species are preferred, heterologous signal sequences, i.e. those originating from other plant species or of microbial origin, may be used as well. Such signal sequences are known to those skilled in the art. Appropriate signal sequences which may be used within the context of the present invention are disclosed in Walter, P. and Blobel, G. (1986) Biochem. Soc. Symp., 47, 183; Von Heijne, G. (1986) J. Mol. Biol., 189, 239; and Sijmons, P. C., Dekker, B. M. M., Schrammeijer, B., Verwoerd, T. C., van den Elzen, P. J. M. and Hoekema, A. (1990) Bio/Technol., 8, 217.

All parts of the relevant DNA constructs (promoters, regulatory-, secretory-, stabilizing-, targeting- or termination sequences) of the present invention may be modified, if desired, to affect their control characteristics using methods known to those skilled in the art.

Phytase activity may be measured according to the method described in the examples below or via a number of assays known in the art. For example, the phytase enzyme activity of the transgenic plant tissue may be tested with an ELISA-assay, Western blotting or direct enzyme assays using calorimetric techniques or native gel assays.

Plants or plant organs containing phytase, as produced via the present invention, may be used in a variety of industrial processes requiring the action of a phytase. Examples of such applications include feed additives for non-ruminants, in soy processing, or in the production of inositol or inositol-phosphates from phytate. They can also be used in other industrial processes using substrates that contain phytate such as the starch industry and in fermentation industries, such as the brewing industry. Chelation of metal ions by phytate may cause these minerals to be unavailable for the production microorganisms. Enzymatic hydrolysis of phytate prevents these problems.

Phytase produced in plants can also be used in a process for steeping corn or sorghum kernels. The plant tissue may be ground before adding to steeping corn. Phytase liberated from the plant tissue can act on phytin, which is present in many corn preparations. Degradation of phytin in steeping corn is beneficial for the added commercial value of corn steep liquor, which is used as animal feed or as a nutrient in microbial fermentations. Furthermore, the degradation of phytin can prevent problems relating to the accumulation of deposits in filters, pipes, reactor vessels, etc. during concentration, transport and storage of corn steep liquor. The action of phytase can also accelerate the steeping process and the separation processes involved in corn wet milling.

The plants or plant organs may be used directly without further processing, or first be processed via conventional means such as grinding to the desired consistency before use. Alternatively, the phytase may be extracted from the plant or plant organ and, if desired, purified before use using conventional extraction methods and purification techniques.

The production of phytases in plants which are compatible with the intended application provides convenience and will reduce production costs as compared to that of microbial phytases in order to allow its economical application, e.g. in animal feed, which eventually will lead to a price/in vivo performance ratio competitive with inorganic phosphate. As a further benefit, the phosphorus content of manure will be considerably decreased. It will be appreciated that the application of phytases, available at a price competitive with inorganic phosphate, will increase the degrees of freedom for the compound feed industry to produce a high quality feed. For example, when feed is supplemented with phytase, the addition of inorganic phosphate may be omitted and the contents of various materials containing phytate may be increased.

In light of the above-mentioned advantages, within the scope of the invention is a monogastric animal feed ration or composition which includes plants or parts thereof from transgenic plant which expresses exogenous phytase. The term feed composition means any compound, preparation, mixture, or composition suitable for or intended for intake by an animal. The composition may include any other ingredient suitable for intake by animals, e.g. comprising sources of protein, lipids, carbohydrates, salts, minerals and vitamins. The ingredients may be selected, and mixed in any proportions, suitable to meet the nutritional needs of the animals to be fed with the feed composition and/or to keep the raw material cost of the feed composition within desired limits and/or to achieve other desired properties of the feed composition. Ingredients are usually selected among, but not limited to, the following materials: plant derived products, such as seeds, grains, leaves, roots, tubers, flowers, pods, husks, oil, soybean meal, soy protein isolate, potato protein powder, wheat, barley, corn, soybean oil, and corn gluten meal; animal derived products, such as fish meal, fish oil, milk powder, skim milk powder, bone extract, meat extract, blood extract, and the like; additives, such as minerals, vitamins, aroma compounds, and feed enhancing enzymes.

The feed composition according to the invention may contain any amount phytase according to the invention suitable to meet the nutritional needs of the animals to be fed with the feed composition and/or to keep the raw material cost of the feed composition within desired limits and/or to achieve other desired properties of the feed composition. The feed ration may contain dried transgenic plants or juice extracted therefrom. Preferably, the transgenic plant is added in quantities sufficient to eliminate the need to supplement the base ration with inorganic phosphorous. In a preferred embodiment the phytase is 10-1000 U/kg of the dry matter of the feed composition, preferably 20-500 U/kg of the dry matter of the feed composition, more preferably 50-150 U/kg of the dry matter of the feed composition. The feed composition may be prepared by any method known in the art, such as agglomeration, extrusion, expansion, or pelleting.

The above-described feed composition may be in any suitable form and administered to the animals in any suitable way known in the art. The term "animals", as used herein, includes all animals. Examples of the animals include non-ruminants and ruminants (such as cattle, sheep and horses). In a particular embodiment the animal is a non-ruminant animal. Non-ruminant animals include mono-gastric animals, e.g. pigs or swine (including, but not limited to, piglets, weaners, growing pigs, and sows); poultry such as turkeys and chicken (including but not limited to broiler chicks and layers); young calves; fish including, but not limited to, fresh water and salt water fish, fish larvae, growing fish, salmon, trout, turbot, sea bass, cod, pollack, sea bream, catfish, halibut, eel, carp; shrimp and sea urchin; and fur animals including, mink and fox.

Currently, in most commercial agriculture, non-ruminant livestock such as swine and poultry are fed mainly grains such as soybeans and maize. Because phytate from these grains is unavailable for absorption, the unabsorbed phytate passes through the gastrointestinal tract, elevating the amount of phosphorus in the manure. Excess phosphorus excretion often leads to environmental problems such as eutrophication. As a result, organic phosphorus makes up about 20-80% of the total phosphorus in soil. The predominant form of organic phosphorus is phytate, which could account for up to half of organic phosphorus in soil (Dalal, 1977, Soil organic phosphorus. Adv Agron 29: 83-117).

On the other hand, phosphorus deficiency in soil is a major constraint for agricultural production worldwide. To promote yield, large amount of phosphorus fertilizers are applied to cropland each year. However, only 10-20% of the fertilizer phosphorus is readily utilized by plants and most fertilizer phosphorus becomes fixed forms in soil that are only poorly available to plants (Vance et al., 2003, New Phytol 157: 423-447). Thus, the large input of phosphorus fertilizer is not only expensive but also nonsustainable. In fact, worldwide resources of rock phosphate are estimated to be depleted by 2050 (Vance et al. 2003).

The above-described transgenic plants have ectopic overexpression of secretory phytase. They can be used not only to acquire phosphorus from phytate in soil, water, and animal waste, but also to redue the amount of phosphorus in animal manure, thereby ameliorating environmental impacts caused by excessive levels of organic P. The approach of overexpressing secretory phytase could be applied to other crops to improve plant nutrient, growth and phytoremediation, and will have significant impacts on sustainable agriculture.

The transgenic plants described herein exhibited several unexpected advantages: (1) the sweet potato sporamin promoter had a high activity in potato; (2) transgenic phytase had high-level expression, high activity, and broad pH ranges; (3) animal feeding tests indicated that transgenic potato tubers containing recombinant phytase were an efficient feed additive; (4) expression of secretory phytase in transgenic potato improved phosphorus utilization and increased size, number, and yield of potato tubers when organic fertilizers containing phytate was used as a sole phosphorus source.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Sweet Potato Sporamin Promoter was Active in Various Organs of Transgenic Potato Potato cultivar *Solanum tuberosum* L. cv. Kennebec was used in this example. Potato stem segments of 2-3-cm long were cultured for initiation of seedlings on an MS agar medium (Murashige-Skoog basal salts, SIGMA) and for production of microtubers on a modified MT agar medium containing MS salts with 5 mg/L 6-BAP and 8% sucrose (Wang et al., American Potato J 59: 33-37). MS salts contain phosphate (170 mg/L or 1.25 mM $KH_2PO_4$). Potato cultures were maintained at 25° C. with a 16-hour daily light.

Plasmids were constructed according to the method described in US Application Publication US 20050198703. Briefly, a DNA fragment containing an 1131-bp SPO promoter sequence (SEQ ID NO: 2) plus a 63-bp signal peptide sequence and an extra 48-bp sequence were PCR-amplified using sweet potato genomic DNA as a template. The primers used were Spo5': 5'-CCCAAGCTTTGCCAAACAGAGC-CTA-3' (SEQ ID NO: 12) and Sposp3': 5'-GGAATTCG-GCGGGTTCGTGTGTGGT-3' (SEQ ID NO: 13). The primers were designed based on the genomic DNA sequence of SPO-A1). The nopaline synthase gene (Nos) terminator was PCR-amplified using pBI221 (CLONTECH) as a DNA template and oligonucleotides 5'-TCCGAGCTGCAGATCGT-TCAAACATTT-3' (SEQ ID NO: 14) and 5'-AGCGAGCTC-GATCGA TCTCTAGACAT-3' (SEQ ID NO: 15) as primers. The 1.24-kb *E. coli* phytase gene appA was PCR-amplified using plasmid pET-appA (Golovan et al., 2000, Can J Microbiol 46: 59-71) as a DNA template and appA 5': 5'-AAA-GAATTCCAGAGTGAGCC GGAGCTGAAGCT-3' (SEQ ID NO: 16) and appA 3': 5'-AAACTGCAGTTACAAACTG-CACGCCGGT AT-3' (SEQ ID NO: 17) as primers.

The SPO promoter was digested with HindIII-EcoRI and inserted into HindIII-EcoRI sites in pBluescript (STRATE-GENE), generating pBS-Sposp. A Nos terminator was digested with PstI-XbaI and fused downstream of the SPO promoter in pBS-Sposp, generating pBS-Sposp-Nos. The appA gene was digested with EcoRI-PstI and inserted into same sites in pBS-Sposp-Nos, generating pBS-Sposp-appA-Nos. The Sposp-appA-Nos fusion gene was excised from pBS-Sposp-appA-Nos with XbaI-HindIII and inserted into same sites in the vector pCAMBIA2301 (a gift from Richard A. Jefferson, CAMBIA, Australia), generating pSpo-appA (FIG. 1). This pSpo-appA contained a CaMV35S-GUS cDNA fusion gene derived from pCAMBIA2301. It contained the SPO promoter-signal peptide sequence (SP)-appA-Nos terminator (3') fusion gene. The CaMV35S promoter-NptII-CaMV35S 3' was used as a selection marker. The CaMV35S promoter-GUS (containing CAT intron)-Nos 3' was used as a selection reporter. The CAT intron could prevent GUS expression in *Agrobacterium* and ensured GUS expression only in transgenic potato.

The resulting plasmid was used to transform potato according to the method described in US Application Publication US 20050198703. Briefly, cultured potato microtubers were sliced into 2-mm thick discs. The discs were placed on a 3C5ZR agar medium (Sheerman et al. 1988, Plant Cell Reports 7: 13-16), co-cultured with 5 mL of *Agrobacterium* in a 3C5ZR liquid medium, and incubated at 26° C. for 15 minutes. The microtuber discs along with *Agrobacterium* were then transferred to a 3C5ZR-AS agar medium, which contained 100 μM acetosyringon (ALDRICH) and 3 g/L phytagel (SIGMA), pH 5.2, and incubated at 28° C. in the dark for 72 hours. The infected microtuber discs were washed three times with a 3C5ZR liquid medium containing 100 mg/L ticarcillin/clavulanic acid (timenten) (DUCHEFA), blotted dry on sterile filter papers, and transferred to a 3C5ZR agar medium containing 100 mg/L each of kanamycin (SIGMA) and timenten and incubated at 26° C. with 16-hour daily light for selection of transformants. The tissues were sub-cultured at weekly intervals.

After several weeks, young shoots formed from the inoculated microtuber discs were transferred to an MS agar medium containing 100 mg/L each of kanamycin and timenten and incubated at 26° C. with 16-hour daily light. Regenerated seedlings were transferred to soil when they were 10-15-cm high and incubated at 26° C. with 16-hour daily light for further growth. Non-transformant lines (NTs) were subjected to the same tissue culture steps as transgenic lines.

Fifteen independent transgenic lines were obtained. They were lines 1-1, 1-2, 1-3, 2-1, 2-2, 2-3, 3-1, 3-2, 3-3, 4-1, 4-2, 6-1, 6-2, 7-1, and 7-2. GUS activity was detected in leaves of all transgenic lines, indicating successful transformation. To determine whether the SPO promoter is capable of directing phytase expression in transgenic potato, transgenic and non-transgenic potato phytase activities were compared. All transgenic lines and non-transformants (NTs) were cultured in a MT medium until microtubers formed.

Assays were conducted to examine phytase activity in total proteins were extracted from microtubers. Protein extract was prepared from microtubers, leaves, stems and tubers according to the method described in Li et al., 1997, Plant Physiol 114: 1103-1111 or Plant Soil 195: 161-169. The phytase activity was determined according to the method described in Shimizu, 1992 Biosci Biotech Biochem 56: 1266-1269. Briefly, 150 µL of extracted proteins were incubated with 600 µL of 1.5 mM sodium phytate at 37° C. for 15 minutes. The reaction was stopped by mixing with 750 µL of 5% trichloroacetic acid. Following production of phosphomolybdate with 1.5 mL of coloring reagent, the liberated inorganic orthophosphate ($P_i$) was photometrically measured at 700 nm. The coloring reagent was prepared freshly by mixing four volumes of a 1.5% ammonium molybdate solution in 5.5% sulfuric acid and one volume of a 2.7% ferrous sulfate solution. One unit of phytase activity was defined as the amount of enzyme that frees 1 µmole inorganic $P_i$ from 1.5 mM-sodium phytate/minutes at pH 4.5 and 37° C. Protein concentration of total soluble proteins was determined by the Bio-Rad Coomassie Protein assay kit.

It was found that phytase activity was barely detectable (6-28 U/g TSP) in microtubers of NTs (6-28 U/g TSP). In contrast, phytase activity was readily detectable (340-630 U/g of TSP) in microtubers of transgenic lines. This result indicates that the SPO promoter is capable of controlling phytase expression in transgenic potato microtubers.

To determine whether the copy number of transgenes affected the expression levels of phytase in transgenic potato, genomic DNA was extracted from leaves and subjected to DNA gel blot analysis. Briefly, genomic DNA was isolated from potato leaves in the manner described Sheu et al. 1996, J. Biol. Chem. 271: 26998-27004. DNA samples (20 µg) were digested with EcoRI, separated by 0.8% agarose gel electrophoresis, and transferred to nylon membranes (MSI). The membrane was hybridized with $^{32}$P-labeled appA DNA probes. It was found that the transgene copy number ranged from 1 to 3 and that the copy number did not correlate with the phytase activity in transgenic potato microtubers.

To determine whether the SPO promoter was active in various organs of transgenic potato, three transgenic lines (1-1, 2-1, and 7-1) were selected for further analysis. Total proteins were extracted from leaves, stems, roots, and microtubers of cultured transgenic potato plants and phytase activity analyzed. Phytase activity was not detected in NTs but was detected in the leaves (36,000-58,000 U/kg), stems (26,000-50,000 U/kg), roots (4000-10,000 U/kg), and microtubers (34,000-38,000 U/kg) of the transgenic lines.

Transgenic potato seedlings were then transferred to pot soil in a growth chamber and allowed to grow for three months. Total proteins were extracted from leaves, stems and tubers and phytase activity analyzed in the manner described above. Phytase activity was not detected in NTs but was detected in the range of 8,000-20,000 U/kg in leaves, 6,000-14,000 U/kg in stems, and 40,000-50,000 U/kg in tubers of transgenic lines. These results indicate that the sporamin promoter conferred phytase expression in various organs of transgenic potato grown either in culture medium or in soil.

To estimate the yield of recombinant phytase produced in transgenic potato, total proteins were extracted from leaves, stems and tubers of transgenic lines 1-1, 2-1 and 7-1 and subjected to protein gel blot analysis using anti-phytase antibodies.

Phytase was overexpressed and anti-phytase antibodies were prepared in the manner described in US Application Publication US 20050198703. Specifically, appA was PCR-amplified using a pET-appA (Golovan et al. Can. J. Microbiol. 46: 59-71) as the DNA template and oligonucleotides 5'-GCGAATTCCAGAGTGAGCCGGAGCTG-3' (SEQ ID NO: 18) and 5'-GCTCTAGATACGCATTAGACAGTTCT-TCGTT-3' (SEQ ID NO: 19) as primers. The PCR products were digested with EcoRI and XbaI, and inserted into same sites in pICZαA (INVITROGEN), generating pPICZαA-appA in which the appA was preceded by an alcohol oxidase (AOX) promoter and α-factor signal peptide. pPICZαA-appA was amplified in *E. coli* strain DH5α (PROMEGA) using a low salt LB broth (1% tryptone, 0.5% sodium chloride, 0.5% yeast extract, pH 7.5) supplemented with Zeocin (25 µg/ml) (INVITROGEN). pPICZαA-appA was linearized by PmeI and transferred into *P. pastoris* strain KM71 (INVITROGEN) by electroporation. The transformed cells were cultured on YPD (1% yeast extract, 2% peptone, 2% dextrose, 1 M sorbitol, pH 7.5) plus zeocin (100 µg/ml) agar plate at 30° C. for 3 days. The Zeocin-resistant yeast colony was incubated in a BMGY medium (1% yeast extract, 2% peptone, 1 mM potassium phosphate, pH 6.0, 1.34% yeast nitrogen bath (INVITROGEN), $4 \times 10^{-5}$% biotin, and 1% glycerol) for enrichment of cell mass and then in a BMMY medium (same ingredients as BMGY medium except that 1% glycerol was replaced with 0.5% methanol) for induction of phytase expression. All media were prepared as suggested in the Easy Select *Pichia* Expression Kit (INVITROGEN). Phytase was the major protein secreted into the culture medium and could be recovered by lyophilization of the culture medium. One hundred micrograms of purified phytase was injected into a New Zealand White rabbit successively at 4-6 intervals for generation of polyclonal antibodies.

To estimate phytase yield, a series of known amounts of purified recombinant appA expressed in *Pichia*, serving as standards, were loaded along with samples from transgenic potato in the protein gel blot analysis. Levels of phytase expressed in transgenic potato were quantified by comparison with the purified phytase standards. The yields of phytase in leaves and stems were approximately 4.2 to 7.4% of TSP, and those in tubers were approximately 2.4 to 3.8% of TSP.

The above results showed that bacterial phytase was produced in transgenic potato tubers at high levels and with high activity under the control of the sweet potato SPO promoter. The high level phytase expression was not associated with copy number of transgene in transgenic potato, indicating that the sweet potato sporamin promoter is highly active in potato. Despite the difference in origins of the potato tuber (a specialized stem) and the sweet potato tuber (a specialized root), these storage organs share many functional and biochemical properties. For example, they both developed as sink organs that accumulate large amounts of reserves, including starch and storage proteins, during the growth of plants. The parallel accumulation of starch and storage proteins, i.e., sporamin and patatin, in sweet potato and potato tubers, respectively, and the inducibility of sporamin and patatin promoter activity in stems of sweet potato and potato, respectively, by sucrose indicate that accumulation of these reserves in tuberous sink tissues are up-regulated by anabolic signals.

In the present study, the SPO promoter conferred high-level phytase expression in microtubers of cultured transgenic potato and in tubers of soil-grown transgenic potato. This suggests that the pathway for transducing anabolic signals to activate sporamin promoter in sink tissues is conserved in potato and sweet potato despite the evolutionary divergence of these two plant species. Phytase activities in leaves and stems from tissue-cultured plants were significantly higher than those in leaves and stems from soil-grown plants. A possible explanation is that, leaves, stems and microtubers from 3-week-old tissue-cultured plants might serve as sink tissues as most nutrients were up-taken by roots from the culture medium; consequently, the sporamin promoter was active in directing phytase expression in leaves, stems and microtubers. In contrast, leaves and stems from 3-month-old soil-grown plants served as source tissues as they provided photosynthetic assimilates to tubers; consequently, the sporamin promoter was more active in tubers than in leaves and stems for directing phytase expression.

EXAMPLE 2

Sporamin Promoter Conferred High-Level Phytase Expression in Transgenic Potato Tubers of Different Sizes A potato plant produces tubers of different sizes. To determine whether phytase expression varied in tubers of different sizes, tubers with sizes ranging from 2 g to 300 g were collected from three plants each of three transgenic lines (1-1, 2-1 and 7-1) and classified into 10 size groups. It was found that phytase activities of most tubers were similar in different groups (in the range of 38,000-59,000 U/kg in Line 1-1 and 43,000-56,000 U/kg in Line 7-1). Phytase activity in Line 2-1 had approximately 20% lower activity at groups 1-6 (ranging 28,000-37,000 U/kg) compared to groups 7-10 (ranging 46,000-55,000 U/kg).

The expression level of phytase was independent of size of transgenic potato tubers indicating that the regulation of sporamin promoter activity was coupled with tuber growth by anabolic signals. Additionally, sight variations in phytase activity were observed in tubers originated from the same transformant after three cycles of propagation and that could be due to physiological conditions of individual plants.

EXAMPLE 3

Phytase Expressed in Transgenic Potato Tubers was Active Over Broad pH and Temperature Ranges The optimal pH and temperature ranges for the phytase activity in transgenic potato were determined. Total proteins were extracted from tubers of transgenic Line 2-1. Optimal pH for phytase activity was measured at 37° C., the temperature in animal gastrointestinal tracks. The activity was examined assayed over a pH range from 1.0 to 6.0. Buffer systems used to create the pH range were: 100 mM Glycine-HCl (for pH 1.0 to 3.5) and 100 mM sodium acetate (pH 3.5-6.0). It was found that the phytase activity reached peaks at pH 2.5 and 5.5. In addition, at least 60% of phytase activity was maintained at pH 1.5 to 6.0.

Phytase active at high temperature may be used to facilitate feed processing. To determine the optimal temperature for the phytase obtained from transgenic potato, total proteins were extracted from tubers of Line 2-1 and analyzed at 35 to 75° C. at pH 5.0. Unexpectedly, it was found that the optimal temperatures for the phytase were between 50° C. to 60° C. It was also found that, at temperatures of 65° C., 70° C. and 75° C., phytase activity were maintained at 80%, 60%, and 50% of the optimal level respectively.

EXAMPLE 4

Over-Expression of Phytase Increased Leaf Pigmentation and Tuber Yield

Plantlets of NT and three independent transgenic lines (Lines 1-1, 2-1, and 7-1) were grown in commercial compost (Potgrond H, Klasmann, Germany) in the farmland of the Taiwan Agricultural Research Institute, Wufeng, Taichung, Taiwan. The compost (70 L/pack) was composed of black sphagnum peat and white peat and supplemented with the following fertilizers: N, 160-260 mg/L; $P_2O_5$, 180-280 mg/L; $K_2O$, 200-350 mg/L; Mg, 80-150 mg/L; KCl, 1.5 g/L. Before planting of potato seedlings, 1% (w/v) of chicken excrement was added to the compost. The phosphorus content in the chicken excrement was 10-15 g/kg, and the final phosphorus content in the compost was 100-150 mg/L. The experimental design was a randomized complete block with four replicates. The plant height, stem number, plant dry weight, and tuber weight and numbers were determined using standard methods. The yield/plant was determined 120 days after transplanting of plantlets into soil. Potato tubers at different sizes (ranging from 2 g to 300 g/tuber) were harvested and analyzed for phytase activity. The transgenic lines 1-1, 2-1, and 7-1 were grown in fields over two winter seasons. Field trials were terminated before plants were completely senescent. Significant differences in phenotypes between transgenic lines and NTs were observed.

First, the leave color and crude leaf extracts of transgenic potato were darker green, which was darker than that of NTs. Specifically, fresh leaves were collected from transgenic potato grown in the compost described above in the farmland and fresh weight determined. These leaves were then ground in liquid nitrogen in a mortar with a pestle. The pigments were extracted with 80% acetone, and light absorption at 331 nm, 470 nm, 552.4 nm, and 556.2 nm were determined using a UV/Visible spectrophotometer. Concentrations of chlorophyll a and b and total carotenoids were calculated in the manner described Lichtenthaler, 1987, Chlorophylls and carotenoids: Pigments of photosynthetic biomembranes. In: Plant Cell Membrane in Methods in Enzymology, Packer, L and Douce, R (ed.), Vol. 148, p. 350-382, Academic Press. Photometric pigment measurement revealed that contents of chlorophylls a and b and carotenoids (including xanthophylls and β-carotene) were 2-3 times higher in transgenic lines than in NTs. Second, the average fresh weight of tubers per plants were larger in transgenic lines 2-1 and 7-1, ranging from 7% ($P<0.05$) to 14% ($<0.01$) in year 1, and in all transgenic lines ranging from 16% to 22% (P<0.01) in year 2 field trials as compared with NTs. See Table 1 below.

TABLE 1

Overexpression of phytase increases yield of potato tubers.

| Line | No. of plant | Total yield of tuber (g) | Average tuber FW per plant (g) | Increase in tuber FW per plant (%) |
|---|---|---|---|---|
| Year 1 | | | | |
| NT | 48 | 18109 | 374.4 ± 55.2 | 100 |
| 1-1 | 47 | 19233 | 396.4 ± 59.8 | 106 |
| 2-1 | 48 | 20583 | 428.0 ± 10.8** | 114** |
| 7-1 | 41 | 16461 | 401.8 ± 41.5* | 107* |
| Year 2 | | | | |
| NT | 70 | 55748 | 774.3 ± 150.7 | 100 |
| 1-1 | 70 | 64232 | 917.6 ± 142.1** | 119** |
| 2-1 | 68 | 66221 | 946.0 ± 90.7** | 122** |
| 7-1 | 72 | 61310 | 901.6 ± 71.0** | 116** |

FW, fresh weight.
*/**Comparisons significantly different to non-transformant (NT) by Dunnett's t-tests at the 0.05/0.01 level.

Transgenic and NT plants grown in year 1 were derived from seedlings propagated in culture media while those grown in year 2 were derived from cuttings of tubers propagated in year 1 and had stronger seedling vigor. Therefore, the average fresh weight of tubers per plant was 2-fold higher for the field trial carried out in year 2 than in year 1.

Third, the tuber number per plant was larger in transgenic lines than NTs, ranging from 1.4- to 1.9-fold (P<0.05) in two field trials. See Table 2 below.

TABLE 2

Overexpression of phytase increases number and size of potato tubers.

| Line | No. of plant | Total no. of tubers | No. of tubers per plant | Ratio (%) of tubers with weight | | |
|---|---|---|---|---|---|---|
| | | | | <50 g | 50~100 g | >100 g |
| Year 1 | | | | | | |
| NT | 48 | 46 | 1 | 28.7 ± 15.5 | 30.9 ± 12.9 | 41.3 ± 9.2 |
| 1-1 | 47 | 69 | 1.5* | 22.9 ± 5.1 | 24.0 ± 14.3** | 53.1 ± 8.9** |
| 2-1 | 48 | 89 | 1.9* | 12.6 ± 2.1 | 22.5 ± 8.8** | 64.9 ± 10.8** |
| 7-1 | 41 | 58 | 1.4* | 24.3 ± 10.8 | 24.4 ± 10.1 | 51.3 ± 13.5** |
| Year 2 | | | | | | |
| NT | 70 | 162 | 2.3 | 22.6 ± 3.4 | 36.1 ± 2.5 | 41.2 ± 5.8 |
| 1-1 | 70 | 275 | 3.9* | 8.8 ± 2.9** | 25.7 ± 5.9** | 65.5 ± 8.0** |
| 2-1 | 68 | 281 | 4.1* | 8.9 ± 1.9** | 23.2 ± 3.9** | 67.9 ± 5.5** |
| 7-1 | 72 | 274 | 3.8* | 8.8 ± 2.4** | 20.0 ± 1.6** | 71.2 ± 3.2** |

*/**Comparisons significantly different to non-transformant (NT) by Dunnett's t-tests at the 0.05/0.01 level.

Tubers were further classified into three groups based on their fresh weights, and relative number of tubers in each group was compared. It was found that the transgenic lines produced more large-size tubers than NTs. In year 1, ratios of tubers with weights 50-100 g each were significantly higher for NT than transgenic lines 1-1 and 2-1 (P<0.01); in contrast, ratios of tubers with weight greater than 100 g each were significantly higher for all transgenic lines than NTs (P<0.01) (Table 2, upper panel). In year 2, ratios of tubers with weights lower than 50 g and 50-100 g each were significantly higher for NTs than for the transgenic lines (P<0.01). In contrast, ratios of tubers with weights greater than 100 g were significantly higher for transgenic lines than NTs (Table 2, lower panel). These studies indicate overexpression of phytase enhanced production and growth of tubers.

EXAMPLE 5

Overexpression of Phytase Improved Phosphorus Acquisition from Phytate

Potato plants grown in field trials were grown in peat moss containing inorganic fertilizer and organic compost. There was a possibility that the increased tuber yield was due to enhanced uptake of phosphorus through hydrolysis of phytate present in organic compost by phytase secreted from transgenic potato roots. To determine whether overexpression of phytase facilitates utilization of phytate as a phosphorus source, NT and transgenic potato seedlings (line 2-1) were grown in phosphate-free MS medium for 1 or 2 weeks, and then transferred to phosphate (1.25 mM $KH_2PO_4$)-containing MS medium or phosphate-free MS medium containing or lacking 0.8 mM phytate for another 2 weeks.

Free phosphorus contents in roots, leaves and stems of transgenic potato seedlings were determined. Pi contents were analyzed according to the method described in Chiou et al., 2006, Plant Cell 18: 412-421 with minor modifications. Fresh tissues were frozen with liquid nitrogen and homogenized with an extraction buffer (10 mM Tris, 1 mM EDTA, 100 mM NaCl, 1 mM β-mercaptoethanol, and 1 mM phenylmethylsulfonyl fluoride, pH 8.0) at a ratio of 1 mg of sample (fresh weight) to 10 μL of the extraction buffer. Samples thus obtained were centrifuged at 13,000 g for 5 minutes, and 60 μL of the supernatant was transferred to a 96-wells plate and incubated at 42° C. for 30 minutes. Each sample solution was then mixed with 140 μL of an assay solution (0.35% $NH_4MoO_4$, 0.86 N $H_2SO_4$, and 1.4% ascorbic acid) and incubated at 42° C. for 30 minutes. The Pi content was measured at $A_{820}$.

No significant difference in free phosphorus concentration was observed between transgenic and NT plants supplied with or without phosphate throughout the entire culture period. For seedlings pre-starved of phosphate for 1 week and then provided with phytate for 2 weeks, free phosphorus concentrations in all tissues examined were not significantly different between transgenic lines and NTs. For seedlings pre-starved of phosphate for 2 weeks and then provided with phytate for 2 weeks, free phosphorus concentrations in leaves of transgenic lines were significantly higher than in NTs (P<0.05). No significant difference in seedling growth rate was observed between transgenic and NT seedlings. However, transgenic seedlings produced more microtubers than NTs, after phytate was added as an extra phosphorus source into the MS medium for 2 weeks. The frequency of cultured seedlings forming microtubers was 48 and 3%, respectively, and that forming microtuber-like organs was both 16% for Line 2-1 and NT. The above result suggests that over-expression of phytase improved phosphorus acquisition from phytate

EXAMPLE 6

Potato-Produced Phytase Improved Phytate Phosphorus Availability to Pigs

Feeding tests with \ pigs were performed to determine whether the phytase produced in potato tubers may function in the stomach and improve phytate-P utilization of pigs.

Tubers of NT and transgenic potato Line 2-1 were sliced and dried at 37° C. for 72 hours. The dried samples were ground to powder and phytase activity was determined in the manner described above. Phytase activity in dried NT and transgenic potato tuber slices were 0.1 and 50 U/g, respectively. Forty crossbred pigs (each weighing approximately 30 kg) were randomly allotted to five group treatments, with 8 pigs per treatment and 4 pigs (half barrows and half gilts) per pen. Treatments consisted of feeding of 4 different dietary phosphorus levels: 0.62% ("Grower-Control"), 0.51% ("Grower-Low P"), 0.56% ("Finisher-Control"), and 0.42% ("Finisher-Low P") for growing and finishing stages. The profiles of the 4 diets are listed in Table 3.

TABLE 3

Composition of experimental diets for animals

| Ingredient | Grower | | Finisher | |
|---|---|---|---|---|
| | Control | Low P | Control | Low P |
| Corn | 635 | 638 | 677 | 680 |
| Soybean meal (43%) | 270 | 270 | 255 | 255 |
| Wheat bran | 30 | 30 | 30 | 30 |
| Fish meal (65%) | 15 | 15 | | |
| Soybean oil | 20 | 20 | 10 | 10 |
| Lysine | 1 | 1 | 1 | 1 |
| Methionine | 0.5 | 0.5 | 0.5 | 0.5 |
| Limestone | 9 | 13 | 9 | 13 |
| Monocalcium phosphate | 12 | 5 | 11 | 4 |
| Salt | 4 | 4 | 4 | 4 |
| Premix[a] | 3.5 | 3.5 | 2.5 | 2.5 |
| Calculated Nutrient composition | | | | |
| ME (kcal/kg) | 3,180 | 3,185 | 3,150 | 3,160 |
| Crude protein (%) | 17.8 | 17.9 | 16.4 | 16.5 |
| Lysine (%) | 1.02 | 1.04 | 0.91 | 0.93 |
| Calcium (%) | 0.79 | 0.78 | 0.71 | 0.71 |
| Phosphorus (%) | 0.62 | 0.51 | 0.56 | 0.42 |
| Ca/P ratio | 1.29 | 1.53 | 1.27 | 1.69 |

[a]Supplied per kg of diet: Fe, 150 mg; Zn, 120 mg; Mn, 50 mg; Cu, 15 mg; I, 2 mg; Se 0.2 mg; vitamin A, 14,000 IU; vitamin $D_3$, 1,200 IU; vitamin E, 44 IU; vitamin $K_3$, 2.4 mg; vitamin $B_1$, 3 mg; vitamin $B_2$, 7 mg; vitamin $B_6$, 3 mg; vitamin $B_{12}$, 0.04 mg; panthothenic acid, 15 mg; niacin 27 mg; folic acid 27 mg; biotin 0.2 mg.

The diets were formulated to have grower and finisher Ca/P ratios of 1.29 and 1.27 for the control group, respectively, and ratios of 1.53 and 1.69 for the low phosphorus group, respectively. The commercial phytase, a recombinant phytase encoded by *Aspergillus niger* phyA, was purchased from BASF (Mount Olive, N.J.) with a specific activity of 5,000 U/g product. Microbial phytase was added as a supplement to the low phosphorus diet at 500 U/kg of feed as suggested by the manufacturer. The potato-produced phytase was supplemented to the low phosphorus diet at two doses of 50 and 150 U/kg of feed. Apart from P, other nutrients were kept constant for all treatments.

Body weight and feed consumption of pigs were recorded every 4 weeks from the start to calculate average daily gain, average daily feed intake and feed efficiency. Serum and feces were collected at the beginning and at the end of the trial for phosphorus analysis. Serum phosphorus contents were determined by an automated chemistry analyzer (KODAK Ektachem DT System), and fecal phosphorus contents were measured by AOAC method (AOAC (1984) Official Methods of Analysis (14th Ed.). Association of Official Analytical Chemists, Arlington, Va.). After the trial, the third and forth metacarpal were collected from all pigs for strength determination (Instron Testing Machine, INSTRON Corp., High Wycombe, Bucks. UK). Data were analyzed as a completely random design with two replicates using the GLM procedure in SAS software (SAS. (1989) SAS/STAT User's Guide (Release 6.12) SAS Inst. Inc., Cary, N.C.). The results were summarized in Table 4 below.

TABLE 4

Effect of dietary microbial and potato-produced phytases on growth performance, serum and fecal phosphorus, and metacarpal bone strength of pigs.

| Items | Control (+P) | Low P (−P) | Microbial phytase (500 U/kg) | Potato-produced phytase (50 U/kg) | Potato-produced phytase (150 U/kg) |
|---|---|---|---|---|---|
| Initial body weight (kg) | 32.7 ± 0.1 | 33.0 ± 0.2 | 32.5 ± 0.1 | 33.0 ± 1.1 | 32.5 ± 0.2 |
| | (100) | (101) | (99) | (101) | (99) |
| Final body weight (kg) | 118.0 ± 2.1 | 113.3 ± 2.5 | 118.9 ± 2.1 | 116.3 ± 2.1 | 118.6 ± 3.6 |
| | (100) | (96) | (101) | (99) | (101) |
| Average daily gain (kg) | 0.76 ± 0.02 | 0.72 ± 0.02[a] | 0.77 ± 0.02[b] | 0.74 ± 0.01 | 0.77 ± 0.03 |
| | (100) | (95) | (101) | (97) | (101) |
| Average daily feed intake (kg) | 2.16 ± 0.09 | 2.11 ± 0.01 | 2.22 ± 0.11 | 2.13 ± 0.11 | 2.13 ± 0.12 |
| | (100) | (98) | (103) | (99) | (99) |
| Feed efficiency (Feed/gain) | 2.83 ± 0.05 | 2.93 ± 0.10[a] | 2.88 ± 0.07 | 2.86 ± 0.11 | 2.77 ± 0.04[b] |
| | (100) | (104) | (102) | (101) | (98) |

TABLE 4-continued

Effect of dietary microbial and potato-produced phytases on growth performance, serum and fecal phosphorus, and metacarpal bone strength of pigs.

| Items | Control (+P) | Low P (−P) | Microbial phytase (500 U/kg) | Potato-produced phytase (50 U/kg) | Potato-produced phytase (150 U/kg) |
|---|---|---|---|---|---|
| Serum phosphorus (mg/dL) | | | | | |
| 0 wk | 10.8 ± 0.9 (100) | 10.2 ± 1.1 (94) | 10.3 ± 1.6 (95) | 10.7 ± 1.2 (99) | 10.6 ± 1.4 (98) |
| 16 wk | 8.0 ± 0.3$^a$ (100) | 6.9 ± 0.4$^b$ (86) | 7.8 ± 0.7$^a$ (98) | 7.6 ± 0.9 (95) | 7.9 ± 1.0$^a$ (99) |
| Fecal phosphorus (%) | | | | | |
| 0 wk | 2.43 ± 0.13 (100) | 2.48 ± 0.15 (102) | 2.60 ± 0.16 (107) | 2.43 ± 0.11 (100) | 2.49 ± 0.17 (102) |
| 16 wk | 2.21 ± 0.08 (100) | 1.92 ± 0.36 (87) | 1.85 ± 0.01 (84) | 1.85 ± 0.09 (84) | 1.90 ± 0.15 (86) |
| Metacarpal bone strength (kg) 16 wk | 182 ± 20$^a$ (100) | 143 ± 14$^{bx}$ (79) | 195 ± 22$^y$ (107) | 162 ± 10$^c$ (89) | 172 ± 9$^y$ (95) |

$^{a,b,c,x,y}$Means within the same row with different superscript differ significantly from each other (P < 0.05). Values in parentheses indicate % of the wild type.

The result indicated that the potato-produced phytase was more effective than the microbial phytase in improving phytate utilization in the animals, even when less potato-produced phytase (50 and 150 U/kg feed) than the microbial phytase (500 U/kg feed) was used. Pigs fed with low phosphorus diet (without inorganic phosphorus supplement) had less average daily gain than the control group (fed with inorganic phosphorus supplement) (P<0.05). The supplement of either microbial phytase or potato-produced phytase recovered the daily gain loss caused by low phosphorus diet. However, there was no difference in average daily gain between treatments with the microbial and the potato-produced phytase. Feed intake was not altered by the dietary phosphorus content or phytase; however, pigs fed with low phosphorus diet with supplement of the potato-produced phytase at 150 U/kg had better feed efficiency (P<0.05) than pigs without phytase supplement. Relative to the control group, the serum phosphorus content in pigs fed with low phosphorus diet fell by 14%, while those in pigs supplemented with either microbial or potato-produced phytase maintained at similar levels at the end of the trial (16 weeks) (P<0.05). The fecal phosphorus content in pigs supplemented with low phosphorus diet, microbial phytase, or potato-produced phytase, fell by 13-16% as compared to the control. Due to the imbalanced Ca/P ratio, low phosphorus group had significantly (21%) lower metacarpal bone strength (P<0.05) as compared to control; however, the mobility of pigs was not affected. The microbial and potato-produced phytase supplements were equally effective (P<0.05) in increasing bone strength, and increasing the level of potato-produced phytase from 50 to 150 U/kg further increased serum phosphorus content and bone strength (P<0.05).

In the above examples, over-expression of phytase led to increase in tuber size, number and yield of field-grown transgenic potato. Several physiological changes observed in the laboratory and field may account for the increase in tuber growth and yield.

First, higher free P concentration was detected in leaves of transgenic seedlings than NTs after pre-phosphate starvation and subsequent application of phytate in culture medium as the sole phosphorus source, indicating overexpression of phytase enhanced phosphorus utilization from phytate by transgenic potato. Since phytase was expressed with the sporamin signal peptide, the recombinant phytase was secreted from roots of transgenic potato and enhanced phosphorus utilization from phytate present in the organic fertilizer.

Second, higher levels of chlorophylls a and b and carotenoids were detected in leaves of field-grown plants, indicating that overexpression of phytase enhanced photosynthesis rate of transgenic potato. In higher plants, these three groups of pigments constitute the major components of the antenna complex for light absorption and energy transfer in the reaction center of the photosynthesis apparatus in chloroplast (Taiz L, Zeiger E (2006) Abscisic acid: a seed maturation and antistress signal. Chapter 23, In: Plant Physiology, 4th edition. Sinauer Associates, Inc., pp. 594-613). phosphorus is an integral component of important compounds of plant cells, including the sugar-phosphate intermediates of respiration and photosynthesis, phospholipids in plant membranes, and nucleotides used in plant energy metabolism (e.g., ATP) and in DNA and RNA. Increase in abundance of these pigments, indicating increase in chloroplast numbers, could have increased the photosynthesis rate of transgenic potato, and consequently more carbon assimilates (sugars) flow from mature leaves into the sink tissues, e.g. growing leaves and tubers. Tuber formation in potato has been shown to be associated with an increase in the photosynthetic rate in leaves. It appears that there is a correlation among phosphorus concentration, photosynthetic rate and tuber yield in potato, which may explain up to 22% increase in tuber yield of transgenic potato was obtained in the present study (Table 1).

Third, an earlier microtuber formation was observed in transgenic potato seedlings than NTs cultured in MS medium (containing 1.25 mM $KH_2PO_4$) with 0.8 mM phytate as an additional phosphorus source, indicating enhanced phosphorus acquisition facilitated microtuber formation. In our field trials, meat moss containing chicken excrement also provided phytate as an additional phosphorus source. As a consequence of improved phosphorus utilization from phytate, increased number, larger size, and higher yield of tubers than NTs were obtained in transgenic potato overexpressing phytase.

The above results indicated that potato-produced phytase has unexpectedly broad pH optima. Phytase stable and active in an acidic environment is essential for the hydrolysis of phytate in animal gastrointestinal tracks. In the present study, the optimal pH for phytase activity in transgenic potato tubers unexpected shifted from an original single peak of 4.5 (Golovan et al., Can J Microbiol 46: 59-71) to a bi-hump peak of 2.5 and 5.5, similar to that seen in germinated transgenic rice seeds (Hong et al., 2004, Transgenic Res 13: 29-39). The phytase in transgenic potato tubers had high activities over the pH range 1.5 to 6.0. One explanation for the high activity at broader pH ranges could be due to structural changes of the bacterial phytase expressed in plants. Three potential glycosylation sites were present in appA phytase, the glycosylation of which could contribute to the shift. The broad and acidic optimal pH profiles of the phytase expressed in potato tubers would allow the enzyme to function well in both the stomach and small intestine of animals, and are essential features for any potential use as feed additives. The temperature optima profiles (50-60° C.) of phytase expressed in potato tubers were similar to the native form phytase, indicating that the shift of pH optima is independent of the thermo-tolerance of the enzyme.

The above results indicate that the potato-produced phytase is at least as effective as commercially available microbial phytase in increasing the bioavailability of phytate-P to weanling pigs. Previous studies indicated that an increase in Ca/P ratio could inhibit pig growth, particularly in terms of average daily gain and feed efficiency (Cera et al. 1988, J. Anim. Sci. 66: 1598-1605; Bertram et al., 1994, ISU Swine Res. Report, pp. 26-29, USA.; Liu et al., 1998, J Anim Sci 76: 808-813). However, in the present study, it was unexpected to find that supplementing either microbial or potato-produced phytase to pigs fed the low phosphorus diet, with Ca/P ratios of 1.53 and 1.69 compared with the control group diet with a Ca/P ratio of 1.27, both average daily gain and feed efficiency were improved. In addition, in comparison with the low phosphorus diet, phytase supplement improved dietary phosphorus utilization, resulting in higher serum phosphorus and better bone strength (Table 4). Therefore, results of the above animal feeding studies indicated that the supplementation of microbial and potato-produced phytase to pigs fed low phosphorus diet improved dietary phosphorus utilization and growth performance. The unexpected lower requirement of potato-produced phytase compared to microbial phytase for diet supplementation could be due to higher specific activity, broader low pH optima, and higher protease resistance, and likely protection by potato tuber tissues in the animal digestive system.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for improving phosphorus uptake by an animal, the method comprising
providing a feed composition containing a transgenic plant, a plant cell thereof, or a plant part thereof; and
feeding the feed composition to the animal to thereby improve phosphorus uptake by the animal;
wherein the transgenic plant, the plant cell, or the plant part contains a heterologous nucleic acid that has a promoter region operably linked to a sequence encoding a polypeptide having phytase activity, the promoter region including the sequence of SEQ ID NO:1; and wherein the polypeptide is expressed in the transgenic plant, the plant cell, or the plant part.

2. The method of claim 1, wherein the animal is a non-ruminant animal.

3. The method of claim 2, wherein the animal is a pig.

4. A method for improving phosphorus uptake by an animal, the method comprising
providing a feed composition containing a transgenic plant, a plant cell thereof, or a plant part thereof; and
feeding the feed composition to the animal to thereby improve phosphorus uptake by the animal;
wherein the transgenic plant, the plant cell, or the plant part contains a heterologous nucleic acid that has a promoter region operably linked to a sequence encoding a polypeptide having phytase activity, wherein the heterologous nucleic acid includes the sequence of SEQ ID NO:2, and wherein the polypeptide is expressed in the transgenic plant, the plant cell, or the plant part.

5. The method of claim 4, wherein the animal is a non-ruminant animal.

6. The method of claim 5, wherein the animal is a pig.

7. A method for improving phosphorus uptake by an animal, the method comprising
providing a feed composition containing a transgenic plant, a plant cell thereof, or a plant part thereof; and
feeding the feed composition to the animal to thereby improve phosphorus uptake by the animal;
wherein the transgenic plant, the plant cell, or the plant part contains a heterologous nucleic acid that has a promoter region operably linked to a sequence encoding a polypeptide having phytase activity, wherein the heterologous nucleic acid includes the sequence of SEQ ID NO:3, and wherein the polypeptide is expressed in the transgenic plant, the plant cell, or the plant part.

8. The method of claim 7, wherein the animal is a non-ruminant animal.

9. The method of claim 8, wherein the animal is a pig.

10. The method of claim 1, wherein the polypeptide having phytase activity includes the sequence of SEQ ID NO: 4.

11. The method of claim 10, wherein the animal is a non-ruminant animal.

12. The method of claim 11, wherein the animal is a pig.

13. The method of claim 1, wherein the polypeptide having phytase activity includes the sequence of SEQ ID NO: 8.

14. The method of claim 13, wherein the animal is a non-ruminant animal.

15. The method of claim 14, wherein the animal is a pig.

16. The method of claim 1, wherein the transgenic plant is a transgenic tuberous plant.

17. The method of claim 16, wherein the animal is a non-ruminant animal.

18. The method of claim 17, wherein the animal is a pig.

19. The method of claim 16, wherein the tuberous plant is a *Solanum tuberosum* plant.

20. The method of claim 19, wherein the animal is a non-ruminant animal.

21. The method of claim 20, wherein the animal is a pig.

* * * * *